(12) United States Patent
Boston

(10) Patent No.: US 7,311,521 B2
(45) Date of Patent: Dec. 25, 2007

(54) INTERPROXIMAL CAVITATION DETECTION DEVICE AND METHOD

(75) Inventor: Daniel W. Boston, St. Davids, PA (US)

(73) Assignee: Temple University of the Commonwealth System of Higher Education, Philadelphia, PA (US)

(*) Notice: Subject to any disclaimer, the term of this patent is extended or adjusted under 35 U.S.C. 154(b) by 356 days.

(21) Appl. No.: 10/965,435

(22) Filed: Oct. 14, 2004

(65) Prior Publication Data

US 2006/0084036 A1 Apr. 20, 2006

(51) Int. Cl.
*A61C 9/00* (2006.01)
*A61C 5/04* (2006.01)

(52) U.S. Cl. .................. 433/37; 433/39; 433/215

(58) Field of Classification Search ............ 433/37, 433/39, 71, 214, 215, 226, 40
See application file for complete search history.

(56) References Cited

U.S. PATENT DOCUMENTS

| | | | | |
|---|---|---|---|---|
| 1,861,645 A | * | 6/1932 | Stein | 433/38 |
| 2,835,628 A | * | 5/1958 | Saffir | 433/39 |
| 3,082,531 A | * | 3/1963 | Jacobson | 433/39 |
| 3,897,796 A | * | 8/1975 | Erickson | 132/321 |
| 4,500,288 A | * | 2/1985 | von Weissenfluh | 433/40 |
| 4,553,936 A | * | 11/1985 | Wang | 433/37 |
| 4,909,736 A | * | 3/1990 | Ritter | 433/39 |
| 5,059,120 A | * | 10/1991 | Lee | 433/37 |
| 5,765,576 A | * | 6/1998 | Dolan et al. | 132/321 |
| 6,244,864 B1 | * | 6/2001 | Fujiwara et al. | 433/71 |
| 6,413,085 B1 | * | 7/2002 | Lee | 433/56 |
| 2004/0152039 A1 | * | 8/2004 | Clegg et al. | 433/39 |

OTHER PUBLICATIONS

T. M. Roberson et al., Sturdevant's Art and Science of Operative Dentistry, 4th Edition, Mosby, St. Louis, 2002, p. 276.
J. B. Summitt et al., Fundamentals of Operative Dentistry, 2nd Edition, Quintessence Publishing Co. Inc., Chicago, 2001, p. 3.
T. M. Roberson et al., Sturdevant's Art and Science of Operative Dentistry, 4th Edition, Mosby, St. Louis, 2002, p. 90.
J. B. Summitt et al., Fundamentals of Operative Dentistry, 2nd Edition, Quintessence Publishing Co. Inc., Chicago, 2001, p. 79.

(Continued)

*Primary Examiner*—John J Wilson
(74) *Attorney, Agent, or Firm*—RatnerPrestia

(57) ABSTRACT

The present invention is direct to a device and method for diagnosis of enamel cavitation of an interproximal dental surface. And in particular, the invention is directed to a device and method for diagnosing enamel cavitation of an interproximal tooth surface that is not visible or probe-able by instrumentation in human permanent and deciduous teeth. More specifically, the device has a substrate of generally rectangular shape and of a sufficient thickness such that it may be inserted into the interproximal space of teeth. On the substrate is disposed an impressionable material for contacting the interproximal surface and forming an impression thereof. The impressionable material has visco-elastic properties such that an impression of enamel cavitation on the interproximal surface remains on the impressionable material following removal of the substrate from the interproximal surface.

20 Claims, 6 Drawing Sheets

OTHER PUBLICATIONS

Ole Fejerskov et al., Dental Caries, The Disease and its Clinical Management, Blackwell, Oxford, 2003, p. 246.

E. S. Akpata et al., Cavitation at Radiolucent Areas on Proximal Surfaces of Posterior Teeth, Caries Research, 1996, 30(5), pp. 313-316.

Mejàre et al., Clinical and Radiographic Appearance of Proximal Carious Lesions at the Time of Operative Treatment in Young Permanent Teeth, Scandinavian Journal of Dental Research, 1986, 94(1) pp. 19-26.

P. A. Rimmer et al., Temporary Elective Tooth Separation as a Diagnostic Aid in General Dental Practice, British Dental Journal, 1990, 169; pp. 87-92.

D. K. Ratledge et al., A Clinical and Microbiological Study of Approximal Carious Lesions, Part 1: The Relationship Between Cavitation, Radiographic Lesion Depth, the Site-Specific Gingival Index and the Level of Infection of the Dentine, Caries Research, 2001, 35(1), pp. 3-7.

* cited by examiner

INTERPROXIMAL CAVITATION DETECTION DEVICE AND METHOD

BACKGROUND OF THE INVENTION

The present invention relates generally to the field of dentistry, and more specifically, to a device and method for diagnosis of enamel cavitation in interproximal carious enamel lesions of teeth.

Enamel carious lesions generally involve decalcification of enamel. Early onset lesions contain macroscopically intact enamel without cavitation on the tooth surface and have the potential for remineralization. Advanced enamel lesions contain a broken, that is, a "cavitated" enamel surface that cannot be repaired by remineralization. Treatment of an advanced lesion thus requires tooth preparation and filling by a trained professional.

The integrity of the outer surface of the tooth is essential for the possibility of remineralization. If the outer surface is intact, it protects the etched inner crystals of hydroxyapatite from being coated by salivary proteins and bacterial plaque. A smooth outer surface also allows the tooth to be cleaned with dental floss to remove plaque. In contrast, a cavitated or carious enamel surface is a surface that is pitted and the top enamel coat is missing. A cavitated surface cannot be readily re-calcified (remineralized) and cannot be readily cleaned of plaque with dental floss.

If the potential cavitated lesion is on a readily-accessible tooth surface, direct visualization or direct physical detection with a dental probe is the preferred techniques to identify whether the lesion contains an intact enamel surface. This technique will not work for interproximal lesions, i.e., lesions occurring on surfaces of a tooth that are between teeth. One technique to diagnose and/or treat an enamel cavitation of an interproximal tooth surface has been to place spacers between the teeth in question prior to diagnosis. These spacers separate the teeth in question and allow a dentist to physically probe the interproximal surface with dental instruments. One drawback to implanting spacers is that some patients may refuse to wear them. Another drawback is that after treatment the teeth must move back together, and this takes time. Additional drawbacks to implanting spacers include the time required for the spacing to develop, which can take hours to days, the limited access gained due to the relatively small amount of resulting tooth movement, discomfort associated with spacer placement, and impaction of food into the resulting spaces after removal of the spacers and before the teeth move back into their original positions.

Another technique to detect an interproximal cavitated surface is through X-rays. Although dental X-rays are useful for detecting the presence of interproximal dental lesions, because the lesions themselves cannot be seen clinically, it is difficult to assess the true condition of the enamel surface to accurately prescribe treatment. Therefore, even with X-rays, it is still difficult to assess the condition of the enamel surface.

What is needed therefore is a rapid, noninvasive, painless and inexpensive but accurate means for detecting and diagnosing cavitation of interproximal surfaces between suspect teeth.

SUMMARY OF THE INVENTION

The present invention is directed to a device and method for diagnosis of enamel cavitation of an interproximal surface that is not readily amendable to probing by instrumentation. More specifically, the device has a substrate of generally rectangular shape and of a sufficient thickness such that it may be inserted into the interproximal space of teeth. Disposed on the substrate is an impressionable material for contacting the interproximal surface and forming an impression thereof. The impressionable material has curing and visco-elastic properties such that an impression of enamel cavitation on the interproximal surface remains on the impressionable material following removal of the substrate from the interproximal surface.

BRIEF DESCRIPTION OF THE DRAWINGS

The invention is best understood from the following detailed description when read in connection with the accompanying drawings. It is emphasized that, according to common practice, the various features of the drawings are not to scale. On the contrary, the dimensions of the various features are arbitrarily expanded or reduced for clarity. Included in the drawings are the following figures.

DETAILED DESCRIPTION OF THE INVENTION

Figure 1:
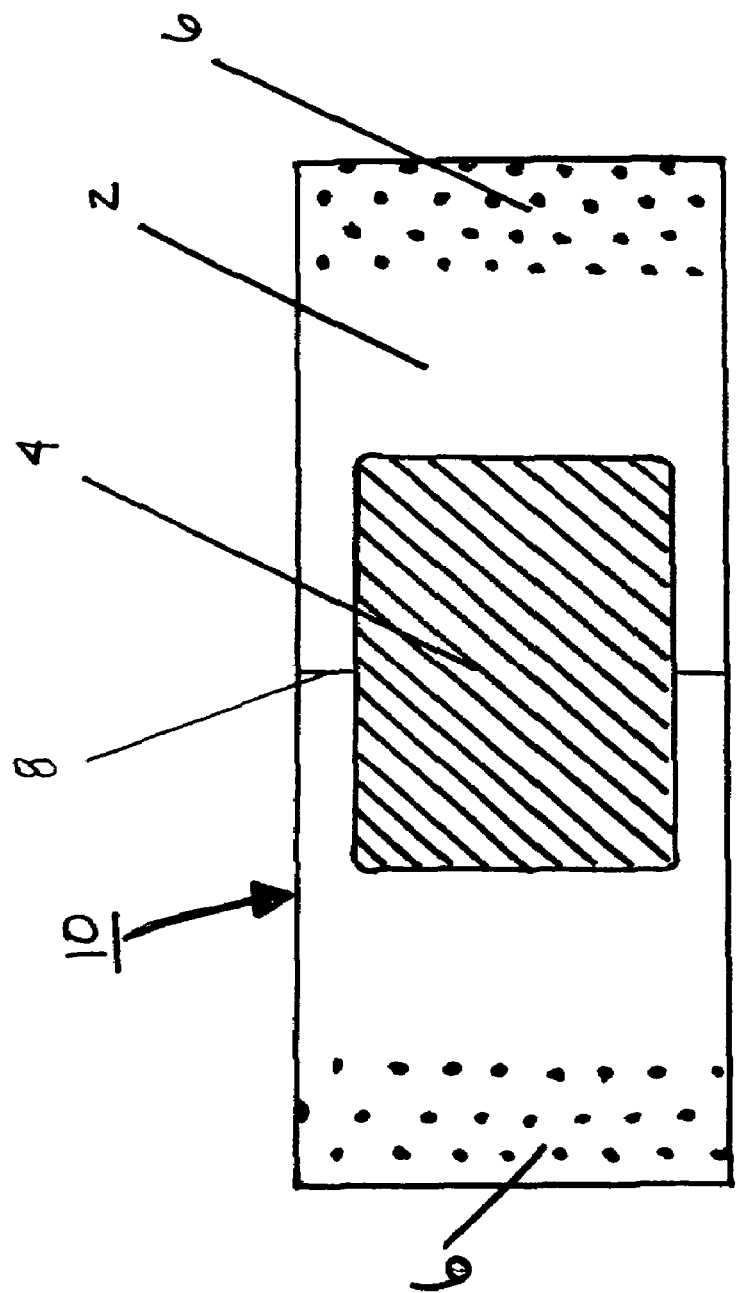
FIG. 1 is a schematic view of an embodiment of the promixal caries cavitation detection device according to the present invention.

The present invention is directed to a device and method for diagnosis of enamel cavitation of an interproximal tooth surface that is not readily amendable to direct inspection or traditional dental probing instrumentation. The device and method are applicable to human permanent and deciduous teeth, as well as veterinary/animal applications. More specifically, the device according to an embodiment of the present invention is a substrate of generally rectangular shape and of a sufficient thickness such that it may be inserted into the interproximal space of teeth. Although a generally rectangular shape for the substrate is preferred, other shapes such as square or butterfly may be used. More importantly, the thickness of the substrate is balanced against the strength and durability of the material that comprises the substrate.

The thickness, or thinness, of the material should be such that the substrate can be inserted between the teeth. In some instances, the interproximal surface to be tested is between two teeth that are completely touching at their respective crown contact areas. The thickness of the substrate, therefore, should allow it to be inserted into interproximal spaces of varying widths, but not be so thin that it cannot support the stress of insertion between teeth and taking an impression of an interproximal surface with the impressionable material.

The substrate may be constructed of any number of materials including fabric, plastic, or metal. The substrate must have sufficient strength to withstand placement between tooth contacts, application to the proximal tooth surface during impressioning, and subsequent removal from the interproximal area. The substrate must have sufficient flexibility to conform to the tooth surface thereby permitting impressioning. When the substrate is fabric, it is preferably a woven fabric such as polyester mesh, nylon, or polyethylene vinyl. The fabric may also be a non-woven fabric, such as a thin film of urethane, polyester, or other suitable polymer film. When the substrate is plastic, it is preferably polyester. When the substrate is metal, it is preferably stainless steel.

The device for diagnosis of enamel cavitation includes an impressionable material disposed on the substrate for contacting the interproximal surface of a tooth in question and for forming an impression thereof. The impressionable material has visco-elastic properties. It can be moldable or it can be pliable until cured. After the impressionable material forms an impression of the interproximal surface in question, the impressionable material must at least partially hold its shape following removal of the substrate from the interproximal surface so that it can be visually inspected for the presence or absence of an impression of an enamel surface defect. The impressionable material may be a curable elastomeric material or a viscous putty-like material that is affixed to, embedded in, disposed on, or integrated into at least one side of the substrate. According to an embodiment of the present invention, the impressionable material covers an area approximately 5×8 mm and is disposed in the middle of the substrate lengthwise and located at the bottom (gingival) vertically.

Suitable visco-elastic materials include wax, and polyvinyl dental putty, such as those sold under the trademark Aquasil Easy Mix Putty Type I Very High Viscosity™ ("Aquasil™"), manufactured by Caulk Dentsply of Milford, Del. If the impressionable material is curable, it may be curable by exposure to specific wavelengths of light, such as those produced by a standard dental composite resin curing light unit, or curable by a chemical reaction. Suitable light-curable materials include polyether and urethane dimethacrylcate resin impression material, polyester urethane dimethacrylate, and copolymer-based temporary dental restorative materials. More preferably, the light-curable material is a single component material for temporary dental restorations such as those sold under the trademark Systemponlay™ manufactured by Ivoclar Vivadent of Amherst, N.Y. Suitable chemical-curable materials include polyether dental impression materials, polyvinyl dental impression materials, or silicone dental impression materials, in high viscosity or putty form. More preferably, the chemical curable material is a material sold under the trademark Aquasil™. Suitable waxes include blends of paraffin and synthetic waxes such as dental rope wax, occlusal indicator wax or dental bite registration wax. More preferably, the wax is a material sold under the trademark Modern Materials Red Boxing Wax™, manufactured by Heraeus Kulzer of Armonk, N.Y.

Some teeth are so close together at their crown contact areas (tight teeth) it is difficult to insert dental floss, let alone a substrate with an impressionable material, between the teeth. To overcome this, according to another embodiment of the present invention, a device for diagnosis of enamel cavitation on an interproximal surface may include at least one semi-rigid leading edge along a substrate to allow the substrate to be initially inserted into the interproximal space when teeth that form the interproximal space are tightly abutted at their respective crown contact areas. The semi-rigid leading edge can be the same material as the substrate, but treated to impart a sufficient stiffness, or the leading edge may be a different material attached to the substrate. For example, the substrate may be made of a polyester fiber mesh fabric and along one edge of the substrate is disposed a thin-plastic edge. To insert the substrate with a semi-rigid leading edge into the interproximal space of tight teeth, the leading edge is first used to penetrate the tight teeth interproximal space. Once initially inserted, the substrate may be slid into proper position by mating the impressionable material with the interproximal surface in question.

A device for diagnosis of enamel cavitation of an interproximal surface of a tooth according to another embodiment of the present invention also includes a substrate having a tactile grip to facilitate handling of the substrate. In one embodiment, the tactile grip is placed at the opposing ends of the rectangular substrate such that it does not interfere with the impressionable material or the leading edge. The tactile grip may be any suitable structure that facilitates handling. For example, the tactile grip may be a textured surface of a substantially similar material as that of the substrate, or a different material disposed on the substrate in a textured pattern. The tactile grip may also be any suitable structure including hooks, tabs, loops, flanges, textured surfaces, tacky surfaces, ridges, and notches each placed on respective opposing ends of the substrate. Preferably, the tactile grip is a textured surface made from a substantially identical material as the substrate.

A device for diagnosis of enamel cavitation of an interproximal surface of a tooth according to another embodiment of the present invention also includes a vertical orientation line on the rectangular substrate placed so as to vertically bisect the area of impressionable material. The vertical orientation line extends to the top edge of the rectangular substrate beyond the impressionable material and provides a visual reference point during final placement of the device into the interproximal space. By knowing the position of the vertical orientation line relative to the contact area at the time of the impressioning procedure and subsequently assessing the relationship of any cavitation impression to the orientation line, the operator can determine the relative position of the cavitation on the tooth surface.

All dental offices should maintain a clean and sterile environment in order to prevent the potential contamination by pathogens from unclean and non-sterile conditions. There are a number of federal regulations and guidelines from the American Dental Association that address this issue. These guidelines generally include the use of hand washing and use of gloves, protective clothing, sterilization and disinfection of instruments, cleaning of dental hand pieces (drills), disposal of waste materials including sharp items, and use of disposable items.

Another embodiment of the present invention comprises a disposable or single-use, pre-sterilized device for diagnosis of enamel cavitation of an interproximal surface of a tooth, which also includes a removable protective layer disposed over and/or around the device. In this manner, multiple pre-made, single-use devices may be stored and made available for easy use. The removable protective layer will maintain the device sterile until the protective layer is removed and the device is placed inside a patient's mouth. Moreover, the device may be sealed within or sandwiched between two protective layers such that the device is made sterile during manufacture, and maintained sterile until its seal is broken for use. The protective layer may also maintain the impressionable surface substantially free of environmental contaminates and air, and facilitates air-curing of the impressionable material when the protective layer is removed.

In accordance with a further embodiment of the present invention, a non-invasive diagnosis procedure is provided, that is, a procedure which does not require opening of the patient's skin, exposure to X-ray, or sedation from pain. The device is used in a method for diagnosing whether an interproximal surface lesion has cavitated by providing a substrate of generally rectangular shape and sufficient thickness for interproximal insertion. The substrate contains an impressionable material disposed thereon for contacting the interproximal surface of the tooth in question and forming an impression thereof. The device is then inserted between adjacent teeth and the impressionable material is mated with the interproximal surface of the tooth in question. Pressure is applied to the impressionable material against the interproximal surface of the tooth in question to form an impression of the interproximal tooth surface by pulling the opposing ends of the substrate at the tactile grip. The direction of applied force is toward the interproximal tooth surface so as to force the impressionable material onto and into any cavitated lesion or unevenness on the tooth surface. After the impressionable material has set, cured, or was exposed to a curing agent, or has formed an impression of the surface without curing such as with wax, the substrate is carefully removed such that the impression formed is not destroyed. Finally, the attending dentist or hygienist evaluates the resulting impression to determine whether or not the lesion is cavitated and/or treatable with restorative filling procedures or with remineralization treatment such as fluoride application.

The impressionable material may posses other qualities to aide in the visual detection of an impression made by a cavitated lesion. According to one embodiment, the portion of the substrate to which the impressionable material is affixed contains a printed pattern. In this embodiment, the impressionable material, when in a uniform thickness, appears translucent or transparent and allows the printed pattern on the substrate to be only partially seen due to the optical filtering effect of the overlying impressionable material. After the impression is taken, the thickness of the impressionable material changes (due to an impression of a cavitated lesion creating a thicker area and thinning in areas where there is no cavitated lesion). The areas of the impressionable material that have increased in thickness are less transparent and now more fully obscure the printed pattern on the substrate. The areas of the impressionable material that have decreased in thickness are more transparent and now more fully reveal the printed pattern on the substrate. Alternatively, the substrate may be made from a fine "fuzzy" material embedded with wax. This means that the substrate is made from a material that has fine filaments, e.g., microfiber synthetic felt. When the fibers of the substrate are undisturbed, the surface of the substrate is uniform. When the impressionable material forms a mold of a cavitated lesion, the fine filaments of the "fuzzy" substrate are disturbed and are no longer uniform, enhancing visualization of the impression of the cavitated lesion.

Yet a further embodiment of the device for diagnosis of enamel cavitation includes a thin film material that changes color in response to pressure. When pressure is applied to the thin material according to this embodiment, the lack of surface pressure in areas where the interproximal surface has cavitated will not cause a change in color of the material whereas surface pressure on the intact interproximal surface area and at the margin of the cavitated area will cause a change in color of the material applied to that area. Pressure can be applied by creating tension to the device itself as it is adapted to the interproximal tooth surface or by rubbing the back surface of the material with the thin blade of a dental hand instrument while the device is adapted to the interproximal tooth surface. Suitable pressure sensitive materials include tactile pressure indicating or measuring films. More preferably, the pressure sensitive materials are those materials manufactured under the trademark Pressurex Tactile Pressure Indicating Film, Micro Film Type™, with pressure range 2-20 psi, manufactured by Sensor Products, Inc. of East Hanover, N.J.

Referring now to the figures where like numerals represent like features, FIG. 1 shows a diagnosis device 10 of generally rectangular shape having opposing ends. Disposed on, affixed to, or integrated with substrate 2 is impressionable material 4. Impressionable material 4 may be disposed substantially equidistant from all sides of substrate 10 or disposed closer to an edge. Above impressionable material 4 is vertical orientation line 8. Vertical orientation line 8 extends beyond the impressionable material to the edge of the substrate to provide a visual reference point for final placement of the device over an interproximal surface. Although FIG. 1 shows the visual reference as a vertical orientation line 8, other visual indicators to assist a dentist in orienting the device are contemplated. For example, the visual indicator may be a change in color of the substrate or a change in shape of the substrate. There is also shown in FIG. 1, tactile grip 6. Tactile grip 6, according to this embodiment, is shown as a perforated or raised textured surface positioned at each opposing end of substrate 2. The impressionable material is shown as being centered with respect to the longitudinal edges, but may be offset toward or along one of such edges to conform to the position of the lesion of which an impression is to be taken.

Figure 2:
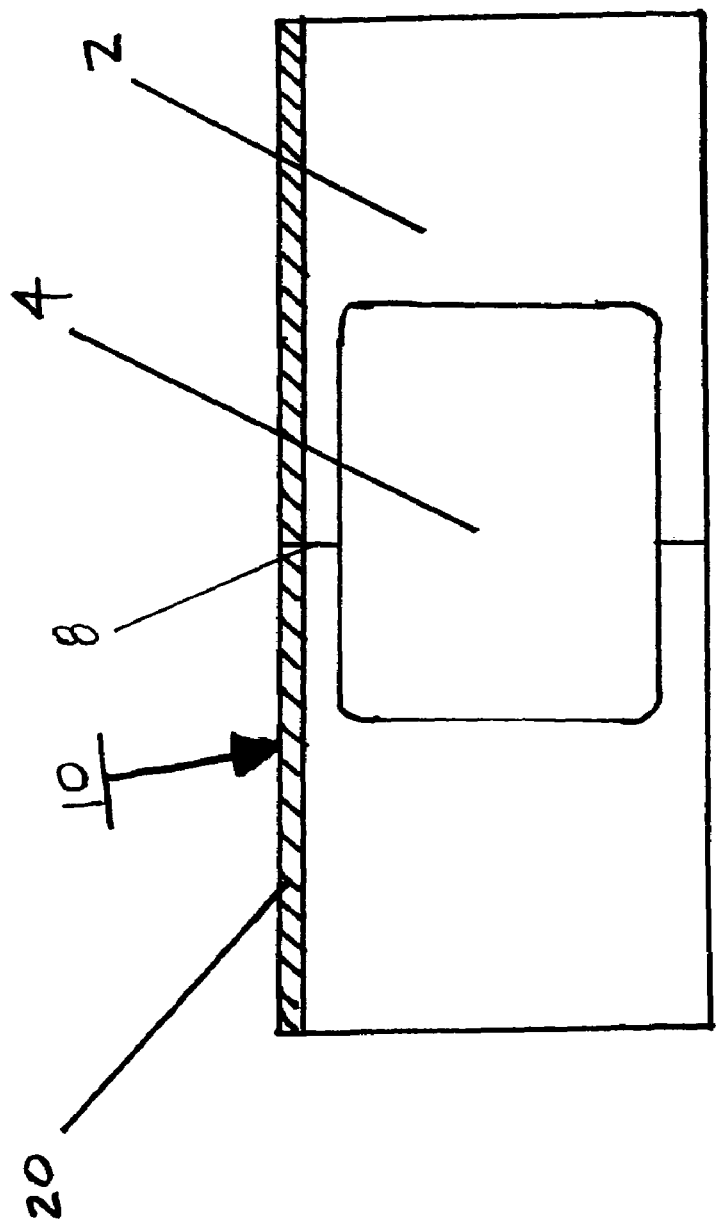
FIG. 2 is a schematic view of another embodiment of the promixal caries cavitation detection device according to the present invention.
Figure 3:
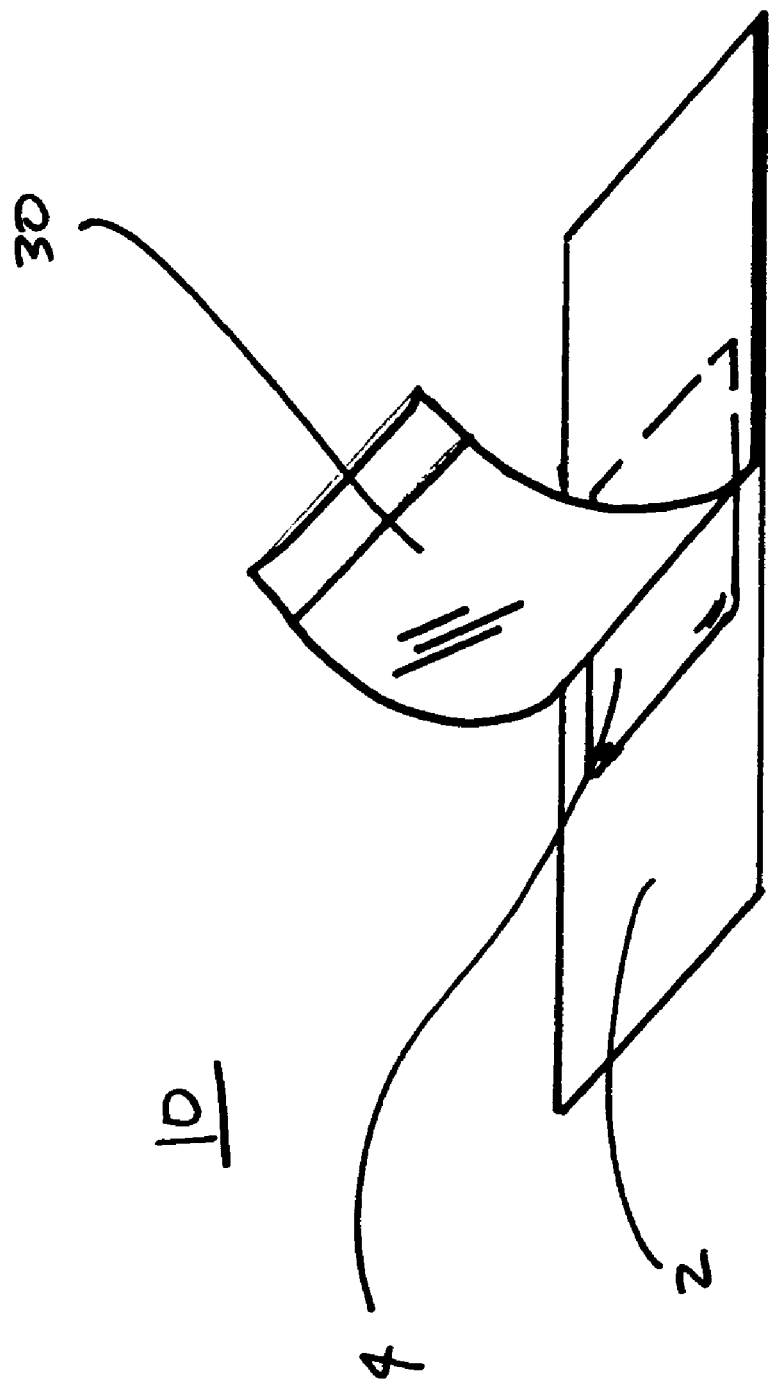
FIG. 3 is a schematic view of yet a further embodiment of the promixal caries cavitation detection device according to the present invention.

FIG. 2 illustrates a diagnosis device 10 including impressionable material 4 disposed on substrate 2. A leading edge 20 is disposed on at least one edge of substrate 2. In this embodiment, leading edge 20 is a hardened area along one edge of substrate 2. The hardened edge facilitates insertion of device 10 into the interproximal space between teeth. FIG. 3 illustrates an embodiment of diagnosis device 10 having a protective layer 30 partially removed so as to expose impressionable material 4 and substrate 2.

Figure 4:
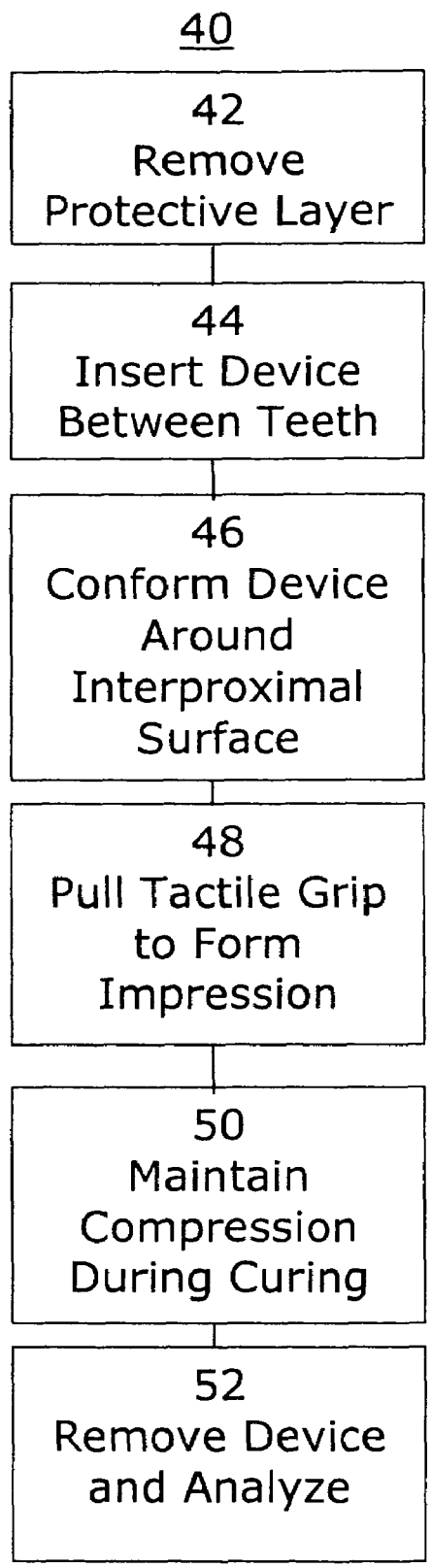
FIG. 4 is a flow chart of an exemplary method of using the proximal caries cavitation detection device according to the present invention.
Figure 5:
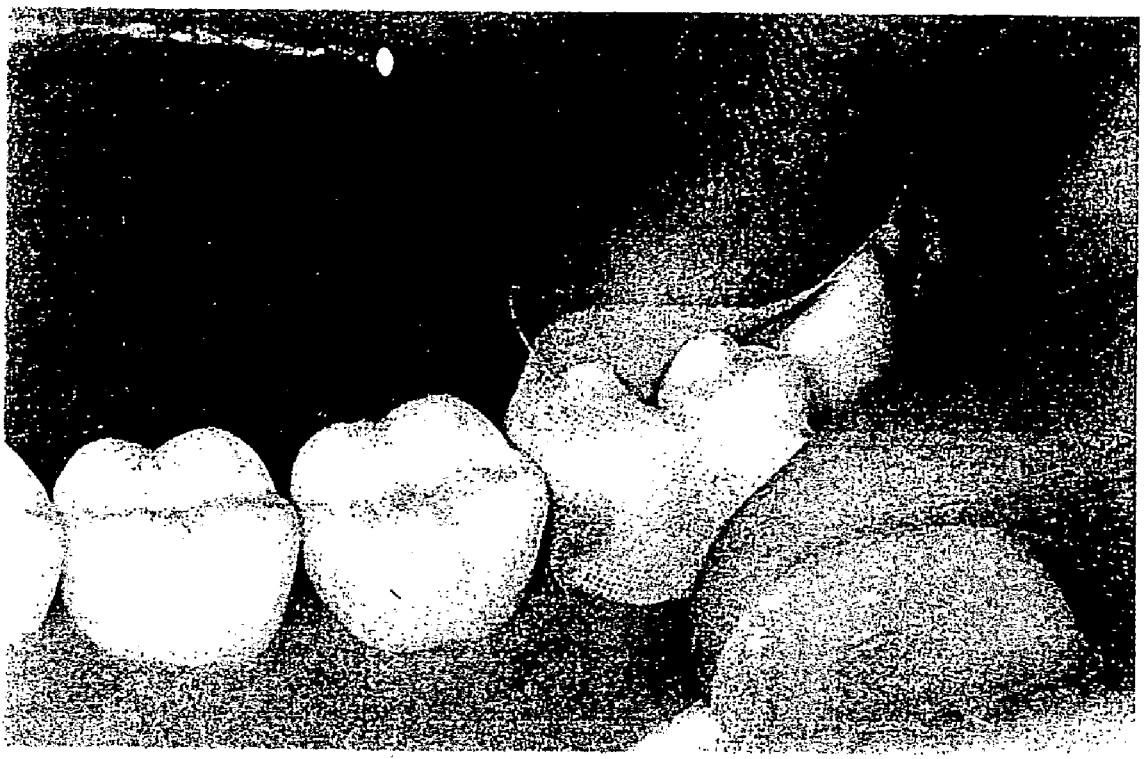
FIG. 5 illustrates an embodiment of a proximal caries cavitation detection device in use.
Figure 6:
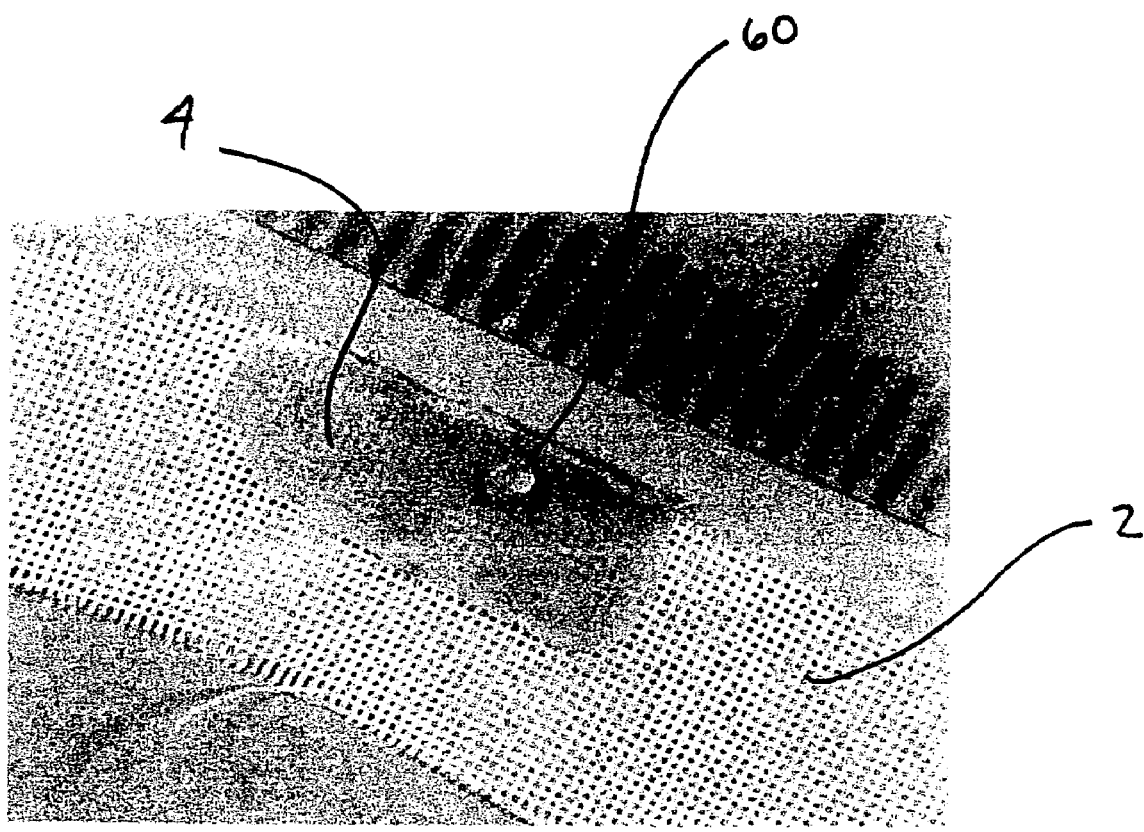
FIG. 6 illustrates an embodiment of a proximal caries cavitation detection device with an impression of a cavitated tooth formed on an impressionable surface.

FIG. 4 is a flow chart 40 representing an embodiment of a method for using the diagnosis device for detection of enamel cavitation in teeth. According to the embodiment of the method shown in FIG. 4, a protective layer is removed from the device shown by box 42, and inserted between the teeth in question shown by box 44. The impressionable material is aligned with the interproximal surface in question shown by box 46 and the substrate is conformed around the tooth shown by box 48 as shown in FIG. 5. Pressure is applied to the impressionable material by pulling on the tactile grips (also shown in FIG. 5) such that the impressionable material forms an impression of the interproximal surface. Compression of the impressionable surface is maintained until a sufficient mold of the interproximal surface is transferred to the impressionable material shown by box 50. FIG. 6 illustrates the resulting device when it is carefully removed from the interproximal space shown in FIG. 4 as by box 52. As shown by FIG. 6, the resulting impression 60 of the impressionable material 4 is analyzed.

EXAMPLES

The following example illustrates a process for preparing the diagnosis device and its method of use as claimed and described herein.

Example 1

A Columbia™ typodont artificial teeth and jaw model showing a distal surface with a simulated cavity created with a #4FG bur was used to replicate a human mouth. A polyester fabric strip was cut to size of 7×70 mm to serve as the substrate.

Polyvinyl putty was applied to the substrate by placing a 0.20 mm thick plastic stencil having a 4×9 mm opening on one edge. The open edge of the stencil was aligned with the edge of the substrate strip. A small portion of the putty was placed on the stencil. With the standard microscope slide held at a sharp angle, the putty was applied to the substrate by dragging the microscope slide across the stencil opening. A resulting 4×9 mm and 0.20 mm impressionable surface was disposed on the substrate.

Example 2

The following is a prophetic exemplary method for detection of a cavitated interproximal surface from a caries lesion.

The teeth in question are professionally cleaned and polished, including flossing, to remove miscellaneous debris that would interfere with the detection process. The interproximal surface of the tooth in question is then air-dried. A sterile promixal cavitation detection device is removed from its packaging.

With the leading rigid edge, the device is inserted into the interproximal space making sure to avoid premature contact of the impressionable surface against the tooth. The impressionable surface is then aligned with the lesion using a visual indicator by sliding the device laterally thereby bringing the impressionable surface into the interproximal embrasure space and mated therewith. Pressure is applied against the interproximal surface of the tooth with the impressionable material by pulling the ends of the device with equal pressure toward the lesion on the interproximal surface.

If the detection device contains a chemically curable material, a constant force of pressure by the impressionable material against the interproximal surface is maintained until the impressionable material hardens. If the impressionable material is curable by other means, for example, by light, the device is exposed or treated with the appropriate amount of hardening stimulus. If the impressionable material is non-curable the device may be removed immediately after impressioning pressure is applied.

Once the impressionable material has formed an impression of the interproximal surface, the detection device is removed from the interproximal space being careful not to destroy the impression of the interproximal surface. This is particularly important when the impressionable material is a non-resilient material, such a wax, as any unintentional contact of the impressionable material may destroy or disturb the accuracy of the impression. Removal is accomplished by first applying pressure on the device to move it away from the interproximal surface in question by pulling the ends of the device in the opposite direction from that used for impressioning. Next, the device is moved in a gingival direction as far as possible without injuring the gingiva and then sliding the device laterally to remove the impressionable surface from the interproximal area. Finally, the device is moved upward occlusally or incisally to remove it from the contact area. After the detection device is safely removed, the resulting impression can be evaluated visually to determine whether the lesion has cavitated. If the lesion has cavitated, the impressionable material will have formed a negative mold of the irregular surface of the inside of the cavity. If the interproximal lesion has not cavitated, the impressionable material will appear flat, that is, it would have a smooth surface.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. A device for diagnosis of enamel cavitation of an interproximal dental surface comprising:
   a substrate of generally rectangular shape and sufficient thickness for interproximal insertion; and
   an impressionable material disposed on only one surface of the substrate for contacting the interproximal surface and forming an impression thereof, wherein the impressionable material comprises a light-curable material selected from the group consisting of polyether and urethane dimethacrylate resin impression material, polyester urethane dimethacrylate, and copolymer-based temporary dental restorative material, the impressionable material being affixed to or embedded in one side of the substrate and having visco-elastic properties whereby an impression of the enamel cavitation of the interproximal surface remains on the impressionable material following removal of the substrate from the interproximal surface, and said substrate having an area free of said material for interproximal insertion between adjacent interproximal surfaces.

2. The device according to claim 1, wherein the substrate is selected from the group consisting of fabric, plastic, a metal material, and mixtures or combinations thereof.

3. The device according to claim 2, wherein the substrate is nylon or polyester fabric.

4. The device according to claim 2, wherein the substrate is a plastic selected from the group consisting of polyester, and polyethylene.

5. The device according to claim 2, wherein the substrate is a metal material comprising stainless steel.

6. The device according to claim 1, wherein the substrate has at least one semi-rigid leading edge for initial interproximal insertion of the substrate when teeth that form the interproximal space are abutted at the crown.

7. The device according to claim 6, wherein the at least one leading edge is the same material as the substrate or is a different material than the substrate.

8. The device according to claim 1, wherein the substrate further comprises a tactile grip to facilitate handling of the substrate during insertion and application of pressure when taking an interproximal impression.

9. The device according to claim 8, wherein the tactile grip is a structure selected from the group consisting of hooks, tabs, loops, flanges, textured surfaces, tacky surfaces, ridges, and notches.

10. The device according to claim 8, wherein the tactile grip is a textured surface.

11. The device according to claim 8, wherein the tactile grip is formed from substantially similar material as that of the substrate.

12. The device according to claim 1 further comprising a removable protective layer disposed over at least the impressionable material, the removable protective layer adapted to seal the impressionable material from the environment.

13. The device according to claim 1, further comprising an orientation line disposed on the one surface of said substrate.

14. A device for diagnosis of enamel cavitation of an interproximal dental surface comprising:
- a substrate of generally rectangular shape and sufficient thickness for interproximal insertion, said substrate having an orientation line disposed on the one surface of said substrate, wherein the orientation line extends from an edge of said substrate to the impressionable material, and
- an impressionable material disposed on only one surface of the substrate for contacting the interproximal surface and forming an impression thereof, said material having visco-elastic properties whereby an impression of the enamel cavitation of the interproximal surface remains on the impressionable material following removal of the substrate from the interproximal surface, and said substrate having an area free of said material for interproximal insertion between adjacent interproximal surfaces.

15. The device according to claim 14, wherein the impressionable material is a visco-elastic material or curable material affixed to or embedded in one side of the substrate.

16. The device according to claim 15, wherein the impressionable material is a visco-elastic material selected from the group consisting of wax and polyvinyl dental putty.

17. The device according to claim 15, wherein the impressionable material is a curable material that hardens upon exposure to air, light, or chemical reaction.

18. The device according to claim 17, wherein the curable material comprises a light-curable material selected from the group consisting of polyether and urethane dimethacrylate resin impression material, polyester urethane dimethacrylate, and copolymer-based temporary dental restorative material.

19. The device according to claim 17, wherein the chemical-curable material is selected from the group consisting of polyether dental impression materials, polyvinyl dental impression materials, and silicone dental impression materials in high viscosity or putty form.

20. A non-invasive, method for diagnosing whether an interproximal surface lesion has cavitated, comprising the steps of:
i. providing a substrate of generally rectangular shape and sufficient thickness for interproximal insertion, said substrate containing an impressionable material disposed on the substrate for contacting the interproximal surface of the tooth and forming an impression thereof;
ii. inserting said substrate between adjacent teeth and mating the impressionable material with the interproximal surface of the tooth in question;
iii. applying pressure to the impressionable material against the interproximal surface of the tooth in question to form an impression of the interproximal tooth surface;
iv. removing the substrate after the impressionable material has received an impression of the interproximal surface; and
v. evaluating the resulting impression to determine whether or not the lesion is cavitated and/or treatable by remineralization.

* * * * *